US011864933B2

(12) United States Patent
Paige

(10) Patent No.: US 11,864,933 B2
(45) Date of Patent: Jan. 9, 2024

(54) SYSTEMS AND METHODS FOR VISUALIZING BELOW AN OPAQUE COMPRESSION PADDLE

(71) Applicant: Hologic, Inc., Marlborough, MA (US)

(72) Inventor: Jeffrey Harold Paige, Wallkill, NY (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/969,863

(22) Filed: Oct. 20, 2022

(65) Prior Publication Data

US 2023/0123188 A1    Apr. 20, 2023

Related U.S. Application Data

(63) Continuation of application No. 17/214,178, filed on Mar. 26, 2021, now Pat. No. 11,627,921.

(60) Provisional application No. 63/000,801, filed on Mar. 27, 2020.

(51) Int. Cl.
*A61B 6/04* (2006.01)
*A61B 6/00* (2006.01)

(52) U.S. Cl.
CPC .......... *A61B 6/0414* (2013.01); *A61B 6/0435* (2013.01); *A61B 6/463* (2013.01); *A61B 6/502* (2013.01)

(58) Field of Classification Search
CPC ........... A61B 6/12; A61B 6/0414; A61B 6/06; A61B 6/502; A61B 6/462; A61B 6/588; A61B 6/04
See application file for complete search history.

(56) References Cited

U.S. PATENT DOCUMENTS

| | | |
|---|---|---|
| 2010/0208037 A1 | 8/2010 | Sendai |
| 2015/0282770 A1* | 10/2015 | Klanian ............... A61B 6/0414 378/208 |
| 2019/0090828 A1 | 3/2019 | Dederichs et al. |
| 2019/0209106 A1 | 7/2019 | Bechtold et al. |
| 2020/0060633 A1 | 2/2020 | Radicke et al. |
| 2021/0298696 A1 | 9/2021 | Paige |

FOREIGN PATENT DOCUMENTS

| | | |
|---|---|---|
| DE | 102014206005 A1 | 10/2015 |
| EP | 3073929 A1 | 10/2016 |

OTHER PUBLICATIONS

European Extended Search Report in Application 21165198.9, dated Aug. 9, 2021, 8 pages.

* cited by examiner

*Primary Examiner* — Don K Wong
(74) *Attorney, Agent, or Firm* — Merchant & Gould P.C.

(57) ABSTRACT

A system for imaging a breast includes a gantry and a tube head rotatably coupled thereto. An x-ray source is disposed within the tube head. A support arm is movably coupled to the gantry and includes a breast support platform. An x-ray detector is disposed within the breast support platform and a compression arm is movably coupled to the support arm. An opaque breast compression paddle is coupled to the compression arm. The breast support platform and the opaque compression paddle at least partially define a compression volume for compressing a breast and a camera is arranged to capture images of the compression volume. An image display is at least partially disposed on the system and is configured to display the images of the compression volume captured by the camera.

22 Claims, 13 Drawing Sheets

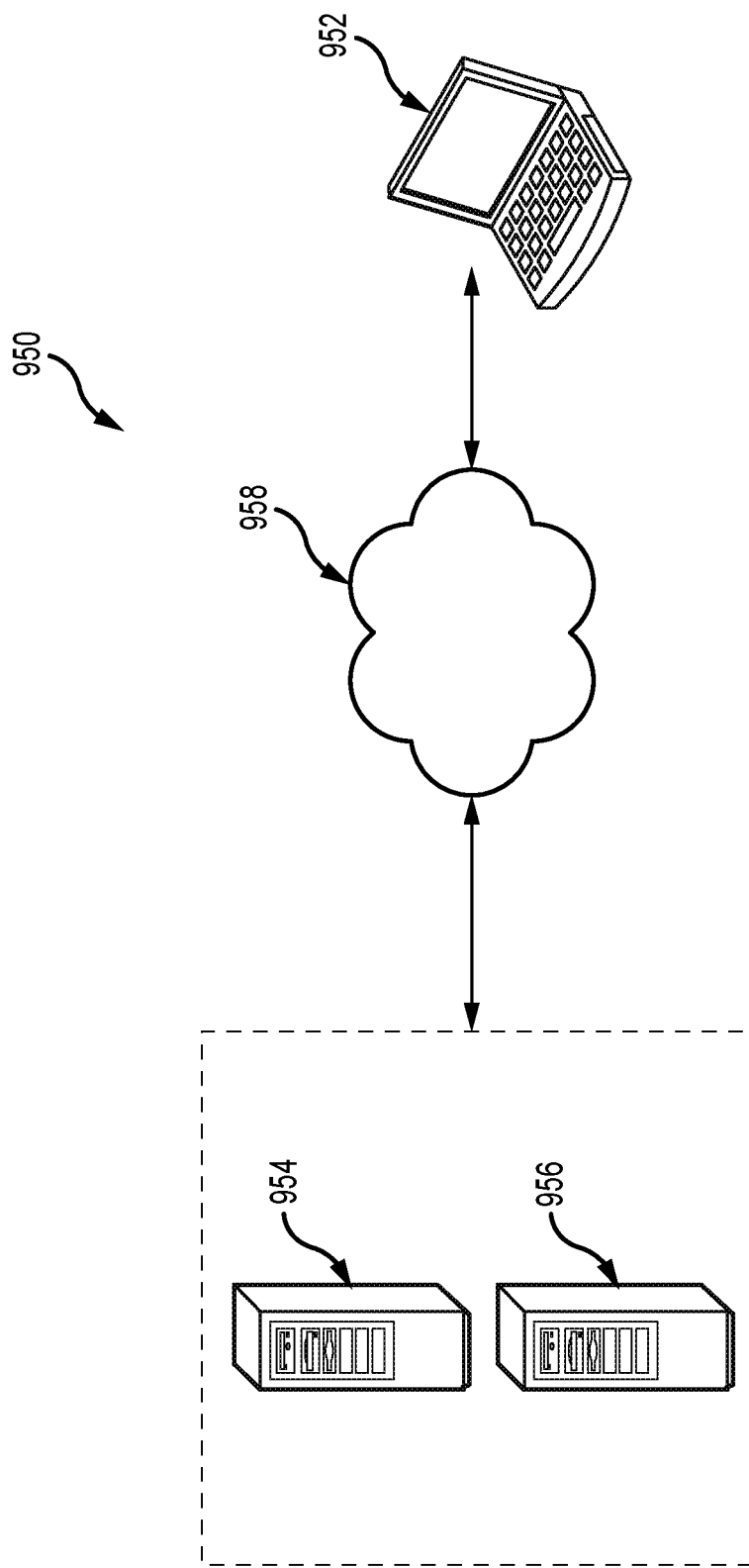

SYSTEMS AND METHODS FOR VISUALIZING BELOW AN OPAQUE COMPRESSION PADDLE

CROSS-REFERENCE TO RELATED APPLICATIONS

This application is a continuation of U.S. patent application Ser. No. 17/214,178, now U.S. Pat. No. 11,627,921, filed Mar. 26, 2021, which claims the benefit of U.S. Provisional Application No. 63/000,801, filed on Mar. 27, 2020, the disclosures of which are hereby incorporated by reference herein in their entireties.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Rigid paddles, or those utilizing a thick compressive foam element, may be utilized in breast imaging procedures. Foam compressive elements, while more comfortable, can greatly reduce visibility of the breast to an x-ray technologist.

SUMMARY

In one aspect, the technology relates to a system for imaging a breast, the system including: a gantry; a tube head rotatably coupled to the gantry; an x-ray source disposed within the tube head; a support arm movably coupled to the gantry, wherein the support arm includes a breast support platform; an x-ray detector disposed within the breast support platform; a compression arm movably coupled to the support arm; an opaque breast compression paddle coupled to the compression arm, wherein the breast support platform and the opaque compression paddle at least partially define a compression volume for compressing a breast; at least one camera arranged so as to capture images of the compression volume; and an image display at least partially disposed on the system, wherein the image display is configured to display the images of the compression volume captured by the at least one camera. In an example, the image display includes at least one of an LED display, an LCD display, and a screen. In another example, the image display includes a screen and the system further includes a projector disposed on at least one of the tube head and the support arm. In yet another example, the screen is substantially convex. In still another example, the at least one camera includes a plurality of cameras.

In another example of the above aspect, at least one camera is secured to at least one of the support arm, the compression arm, and the opaque compression paddle. In another example, the plurality of cameras are distributed along an edge of the compression volume. In yet another example, the projector includes a plurality of projectors. In still another example, the screen is disposed on the compression paddle, along a path of an x-ray emitted from the x-ray source.

In another aspect, the technology relates to a method of displaying an image of a breast in a breast compression system having a breast support platform and a breast compression paddle, the method including: supporting the breast on the beast support platform; imaging at least a portion of the supported breast with at least one camera disposed on the breast compression system; and displaying at least a portion of the image. In an example, the image is displayed on a display. In another example, displaying the image includes projecting the image to a screen. In yet another example, the at least one camera includes a plurality of cameras and wherein the imaging operation includes imaging different portions of the supported breast with the plurality of cameras so as to obtain multiple images. In still another example, the displaying operation includes displaying the multiple images and at least partially overlapping adjacent portions of the multiple images.

In another example of the above aspect, the multiple images include images of at least a top surface and at least a side surface of the breast. In another example, the image is a moving image. In yet another example, the method includes detecting contact between at least a portion of the breast compression paddle and the breast. In still another example, the image is a moving image and wherein the method further includes freezing display of the moving image based at least in part on the detected contact. In another example, the method further includes emitting an x-ray towards the breast and through the screen based at least in part on the detected contact.

In another aspect, the technology relates to an upgrade system for a breast x-ray imaging system including a tube head, a compression assembly, and a compression paddle, the upgrade system including: a camera; a bracket for connecting the camera to the compression assembly; a display for displaying an image obtained by the camera; a securement element for connecting the display to the breast imaging system; and a transmission cable connectable to the camera. In an example, the display includes at least one of an LCD screen and an LED screen, wherein the securement element includes a bracket for connecting the display to at least one of the compression assembly and the compression paddle, and wherein the transmission cable is connectable to the display. In another example, the display includes a projector, wherein the securement element includes a bracket for connecting the projector to the tube head, and wherein the transmission cable is connectable to the projector. In yet another example, a sheet material is securable to the compression paddle.

BRIEF DESCRIPTION OF THE DRAWINGS

FIG. 12 depicts an example of a network in which the various systems and methods disclosed herein may operate.

DETAILED DESCRIPTION

Figure 1A:
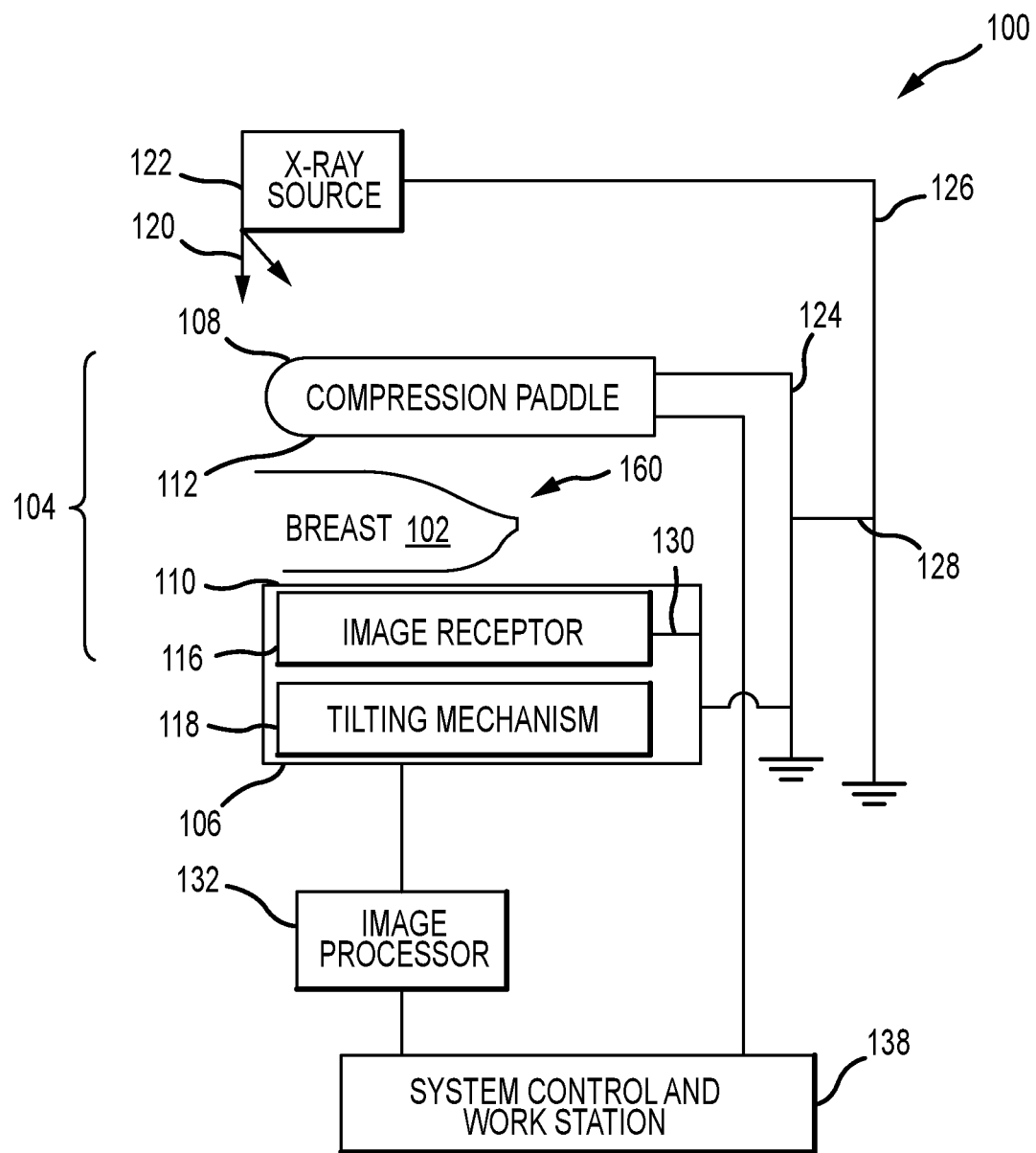
FIG. 1A is a schematic view of an exemplary imaging system.
Figure 1B:
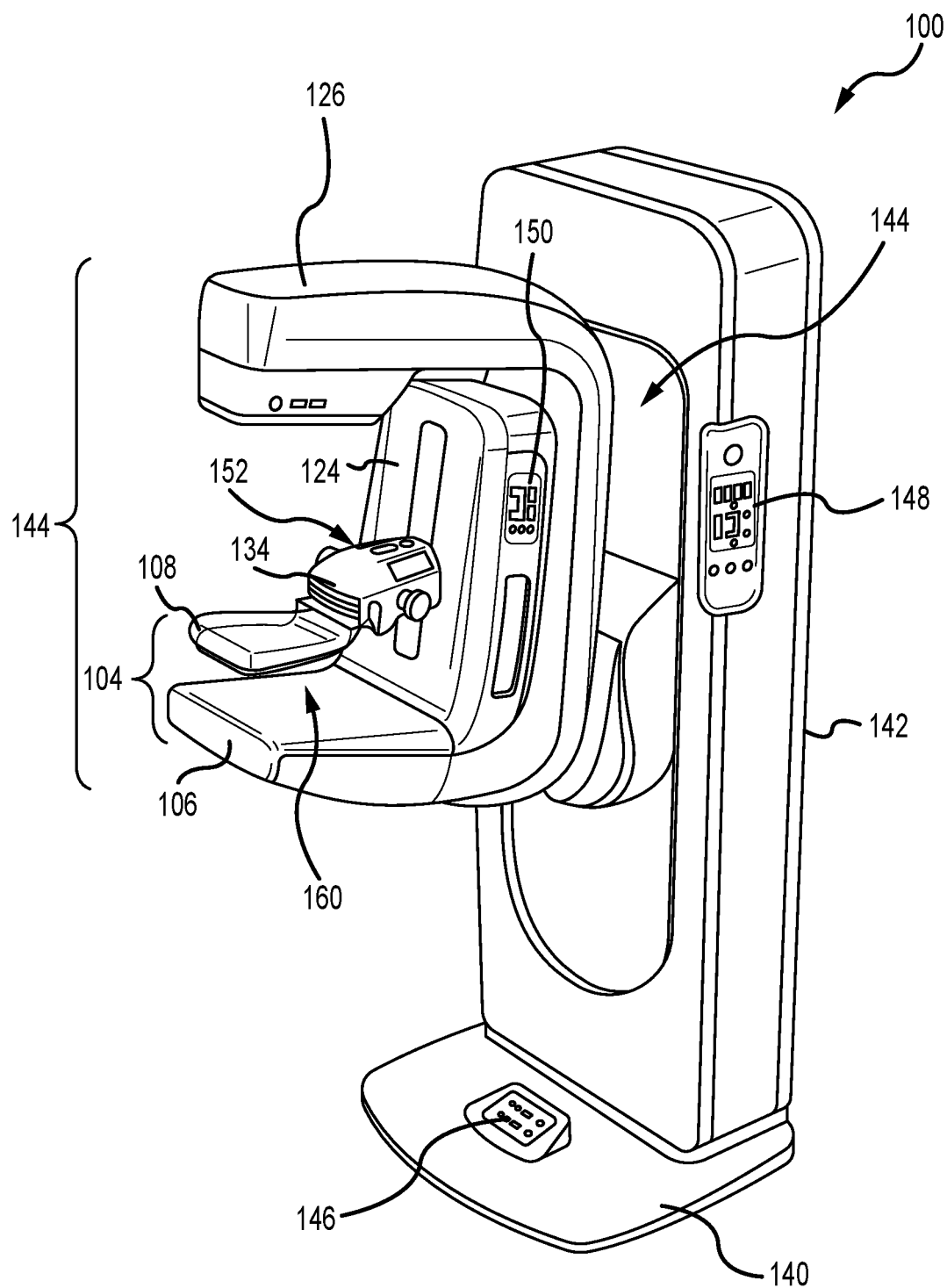
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. Either or both of these compression surfaces 110, 112 may be rigid plastic, a flexible plastic, a resilient foam, and so on. Examples of compression paddles having resilient foam compression surfaces are described herein. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

The imaging system 100 includes a floor mount or base 140 for supporting the imaging system 100 on a floor. A gantry 142 extends upwards from the floor mount 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 144.

A number of interfaces and display screens are disposed on the imaging system 100. These include a foot display screen 146, a gantry interface 148, a support arm interface 150, and a compression arm interface 152. In general the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired. Any of the screen 146, or interfaces 148, 150, and 152 may be utilized with the technologies described further herein to improve visualization of the breast below the compression paddle 108, especially paddles utilizing thick opaque foams as compressive surfaces, which decreases visibility of a breast. Other configurations are further described below.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. This can be particularly challenging for systems 100 that utilize paddles having opaque foams. The opaque foam obscures or even eliminates visibility into the compressive volume 160, defined as the volume between the lowest surface of the compression paddle 108 (or foam compressive element 202) and the highest surface of the support platform 106.

Figure 2:
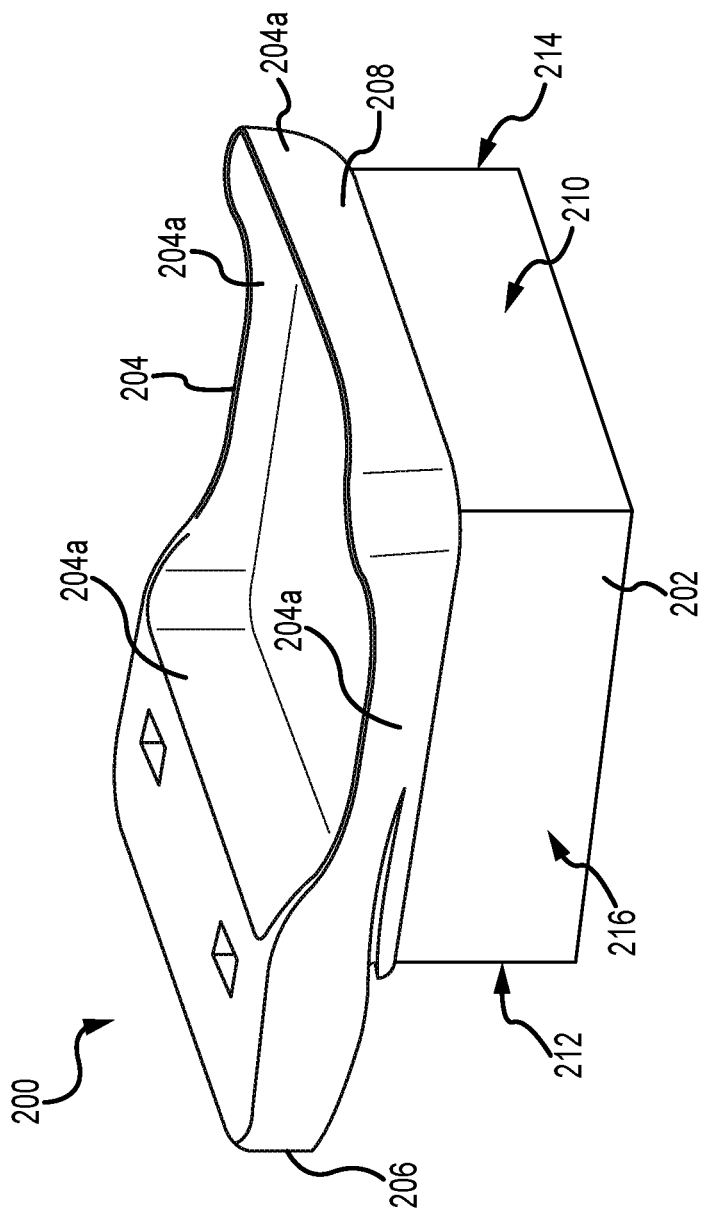
FIG. 2 is a perspective view of a breast compression paddle having a foam compressive element.

FIG. 2 is a perspective view of a breast compression paddle 200 having a foam compressive element 202 secured to a rigid substrate 204. The paddle 200 includes a bracket portion 206, generally integral with the substrate 204 for connecting the paddle 200 to a compression arm of an imaging system. The paddle 200 also includes a leading face 208, opposite the bracket portion 206, which is disposed proximate a chest wall of a patient during compression and imaging procedures. In examples, the substrate may be rigid. As used herein, the term "rigid" does not imply that the substrate 204 is free from bending during compression of a breast, rather that the substrate 204 displays greater resistance to bending or deformation than the foam compressive element 202 secured to a bottom of the substrate 204. Raised walls 204a provide additional rigidity.

The foam compressive element 202 may be secured to a bottom surface of the substrate 204 with mechanical fasteners or chemical adhesives. The foam compressive element 202 includes a number of edge surfaces. A leading edge surface 210 is disposed proximate the leading face 208 of the substrate 204 so as to be disposed proximate the chest wall of a patient during compression and imaging procedures. A trailing edge surface 212 is disposed opposite the leading edge surface 210, proximate the bracket portion 206. Lateral edge surfaces 214, 216 are also depicted. In general, these lateral edge surfaces 214, 216 may be depicted as inner or outer lateral edge surfaces, consistent with terminology typically used to describe inner and outer sides of the breast. Of course, a person of skill in the art will recognize that the same compression paddle 200 may be used to compress either breast, one at a time, which would effectively change the application of the terms "inner" and "outer" to the lateral edge surfaces of the foam compressive material 202. Regardless of specific dimensions, the opaque foam compressive element can block visibility of the breast, thus making positioning thereof difficult.

The technologies described herein utilize a visualization system of one or more cameras used to capture image(s) of a breast as a compression paddle (largely opaque due to the utilization of a thick foam compressive element). These images are displayed in a location proximate the compression paddle, support arm, or other component of the system and thus visible to the technician. The one or more cameras can capture images of discrete locations of the breast (e.g., the nipple, side, upper surface, etc.) and display those areas as discrete images or may combine them into a display that mimics the size and/or shape of the breast. As the technologist grabs and manipulates the breast, the resulting position of the breast will be visible on the display and compression and imaging may then be performed.

Figure 3:
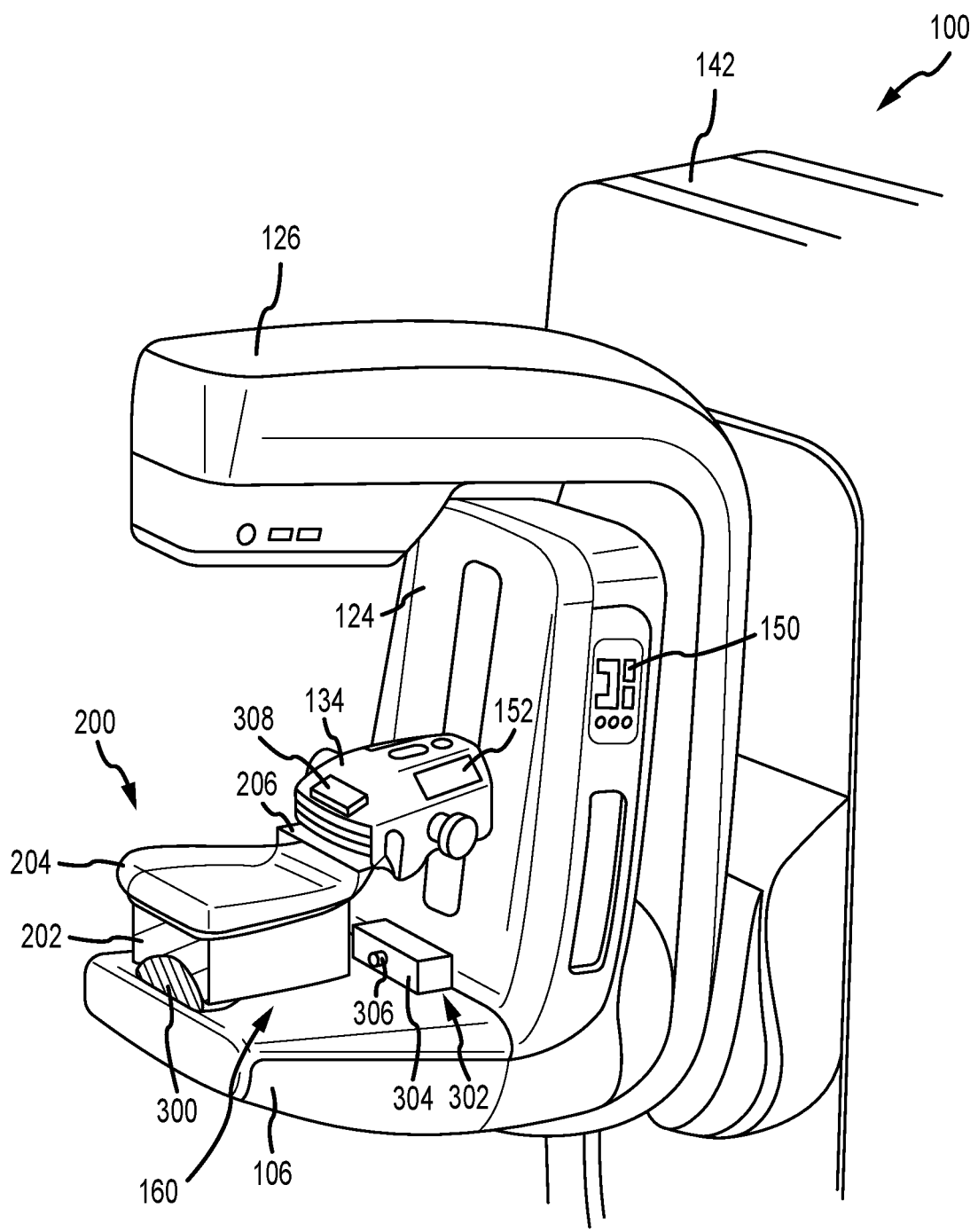
FIG. 3 is a partial enlarged perspective view of an imaging system having an example of a camera imaging and display system.

FIG. 3 is a partial enlarged perspective view of an imaging system, such as the imaging system 100 first depicted in FIGS. 1A and 1B, having an example of a camera imaging and display system. Not every component of the imaging system 100 is depicted in this partial view. The imaging system 100 includes a gantry 142 having rotatably connected thereto a tube head 126. A support arm 124 is separately connected to the gantry 142. A compression arm 134 is movably connected to the support arm 124 and acts as a connection for a compression paddle 200. The compression paddle 200 is connected at a bracket 206 and includes a rigid substrate 204. A foam compressive element 202 is secured to a lower portion of the rigid substrate 204, as described elsewhere herein. Typically, as a breast (a phantom 300 is depicted) is being positioned by a technologist, the technologist will often stand in positions in front of and to the side of the patient (for example, to the left or the right of the support platform 106 and compression paddle 200). For breast imaging procedures using a substantially transparent compression paddle, such a position allows for good access to and visibility of the breast. However, for compression paddles 200 that utilize a foam compressive element 202, visibility is hindered or eliminated. As such, the imaging system 100 includes a camera 302 to capture images of the breast. The camera 302 may be in a discrete housing 304, or may be located within a portion of the support arm 124, or the support platform 106. One or more lenses 306 that increase the field of view of the camera 302 (e.g., fish eye, wide angle, etc.) may be utilized. In the depicted orientation, the camera 302 is located at an interface of a vertical portion of the support arm 124 and the horizontal support platform 106. This location gives good visibility to a forward portion of the breast 300, e.g., the nipple area. The camera 302 may be of a motion capture-type, or may capture still images at predetermined intervals.

The images captured by the camera 302 may be sent to a system control (such as depicted in FIG. 1A), or may be processed by a dedicated system disposed within the camera housing 304 or other component of the imaging system 100. The images may then be sent to a display 308 that may be disposed in various locations on the imaging system 100. In examples, the display may be disposed on the gantry 142, tube head 126, or the support arm 124, in a location conveniently visible to the technologist. In the depicted configuration, the display 308 may be disposed on an upper portion of the compression arm 134. The display may be an LCD or other type of display with sufficient resolution to enable the technologist to easily view the displayed images. The images may be processed as required or desired and displayed in an upright, inverted, mirrored, or other orientation, which may increase usability and acceptance of the display. The orientation of the displayed images may change based on the location of the technologist or other considerations. The technologist may control capture or display of the images at one or more of the interfaces 150, 152, (or interface 148 or screen 146, neither of which are depicted in this figure). In addition, the images may be displayed on any of the interfaces 148, 150, or 152, or screen 146, as required or desired for a particular application. Having a dedicated display 308, however, may desirable.

The camera 302 and display 308 may be discrete units that are battery-powered and may communicate via a wired or wireless connection (such as Bluetooth, Wi-Fi, or other communication system). Either or both of the camera 302 and battery 308 may be battery-powered, or may be powered by the system 100 itself. In the case of battery-powered components that communicate wirelessly, the camera 302 and display 308 may be sold separately or as a kit. Each component may include mechanical, fabric hook-and-loop (sold under the brand name VELCRO), and/or adhesive fasteners that allow the components to be secured to an appropriate location of the system. Such a configuration would enable an existing imaging system 100 to be enhanced as described herein, without requiring an expensive or time-consuming redesign, or downtime of the imaging system.

Figure 4:
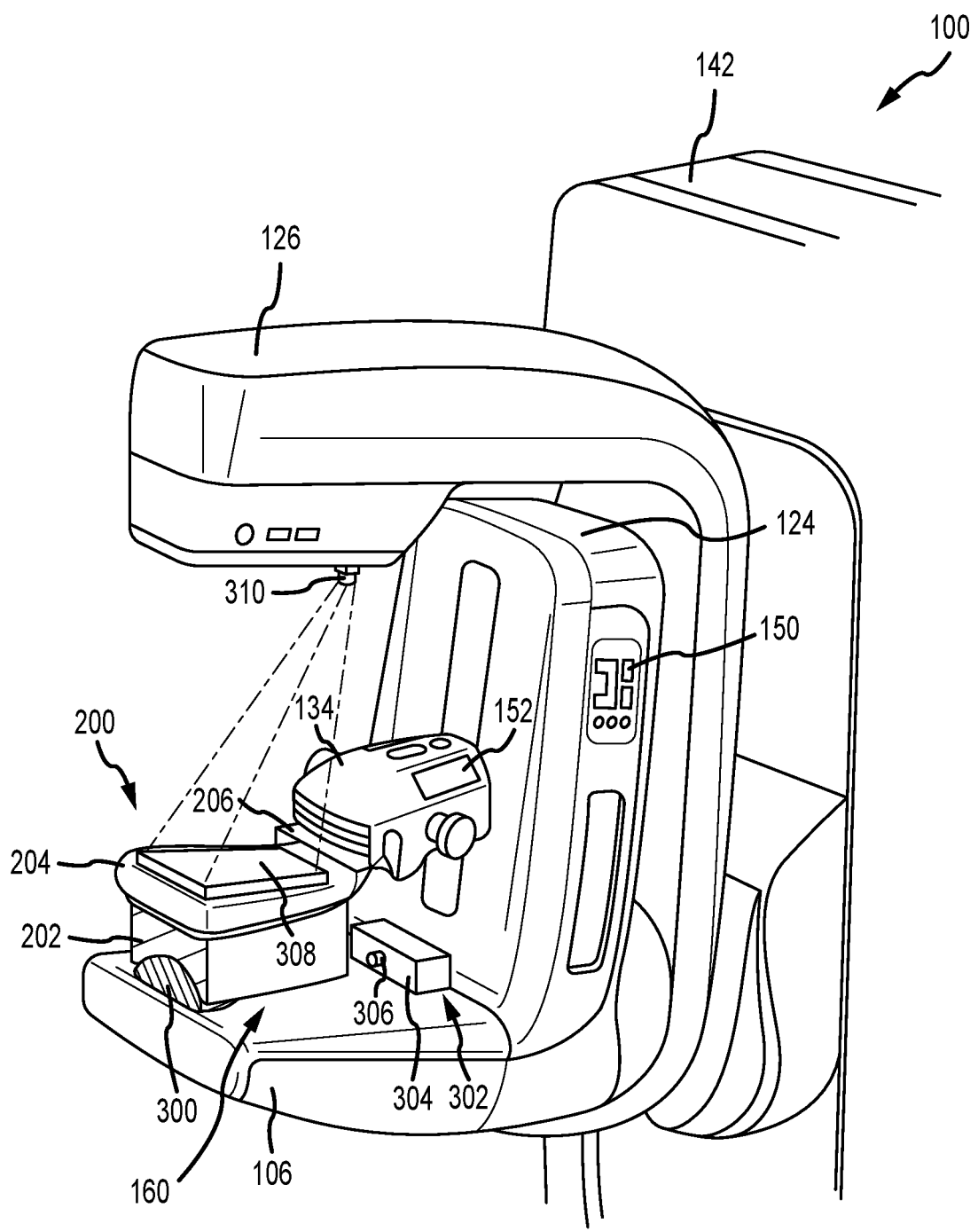
FIG. 4 is a partial enlarged perspective view of an imaging system having another example of a camera imaging and display system.

FIG. 4 is a partial enlarged perspective view of an imaging system, such as the imaging system 100 first depicted in FIGS. 1A and 1B, having another example of a camera imaging and display system. Not every component of the imaging system 100 is depicted in this partial view. Further, a number of components are depicted in FIG. 4, but are described above with regard to other figures; as such, those components are not necessarily described further. A significant difference between the system of FIG. 4 and that depicted in FIG. 3 relates to the type of display 308 utilized. In FIG. 4, the display 308 is incorporated into the paddle 200 itself, as a screen. A projector 310 is disposed on the tube head 126, for example, in a location that is out of the path of the emitted x-ray. In another example, the projector 310 may be disposed on the support arm 124. The projector 310 projects the images onto the screen 308. Since the foam compressive element 202 is opaque, that element may act as the screen 308 itself. Thus, the images are projected onto the surface of the foam compressive element 202. In another example, the rigid substrate 204 of the compression paddle 200 may be formed of an opaque material which may function as the screen 308. In yet another example, the screen 308 may be an opaque film, flexible material, or rigid material that is secured to the rigid substrate 204. Since the screen 308 in FIG. 4 lies within the x-ray emission path, the screen 308 must be radiolucent.

Like the examples depicted above, the various components of the camera and display system of FIG. 4 may be integrated into the imaging system 100 itself or sold as discrete components (e.g., which may be used to improve existing imaging systems). In an examples, a battery-powered and Bluetooth-capable camera 302 and projector 310 may be sold with a discrete screen 308. Each component may be secured to an appropriate location on the imaging system 100 as required or desired.

Figure 5:
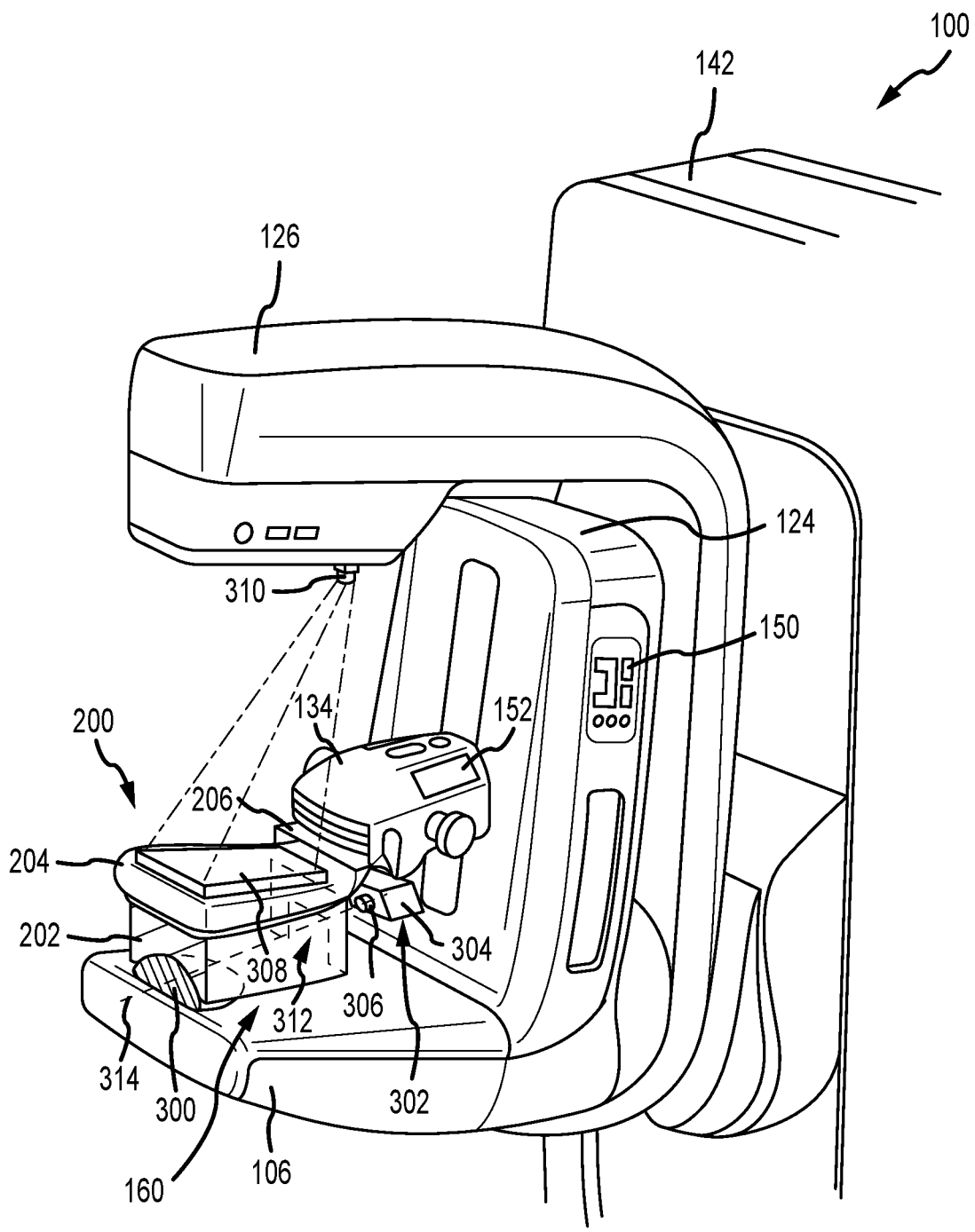
FIG. 5 is a partial enlarged perspective view of an imaging system having another example of a camera imaging and display system.

FIG. 5 is a partial enlarged perspective view of an imaging system, such as the imaging system 100 first depicted in FIGS. 1A and 1B, having another example of a camera imaging and display system. Not every component of the imaging system 100 is depicted in this partial view. Further, a number of components are depicted in FIG. 5, but are described above with regard to other figures. As such, those components are not necessarily described further. The system 100 of FIG. 5 utilizes a projector 310 and display screen 308, as described above with regard to FIG. 4. Notably, however, the camera 302 is mounted to an underside of the compression arm 134 and is again pointed directly at the nipple end of the breast 300. The close proximity to the foam compressive element 202, however, may increase the likelihood that the view of the camera 302 may be blocked. As such, the depicted foam compressive element 202 includes a cut-out 312 or otherwise has a portion of the foam compressive element 202 removed, so that the line of sight 314 from the lens 306 to the breast 300 remains unobstructed. This cut-out 312 may extend along a portion of the compressive element 202 so as to increase visibility of the breast 300 for as long as possible as the compression arm 134 lowers the compression paddle 200. Of course, in any of the configurations depicted herein, the line of sight 314 of the camera 302 may ultimately be obscured by the foam compressive element 202. However, by removing portions of the foam compressive element 202 unlikely to contact the breast 300, line of sight 314 to the breast 300 may be maintained for a longer period of time as the compression arm 134 is lowered towards the breast 300. In another example, the display 308 mounted on the compression arm 204 may be utilized in conjunction with this camera 302 position. This may advantageously allow for a simplified wired connection between those two components.

Figure 6:
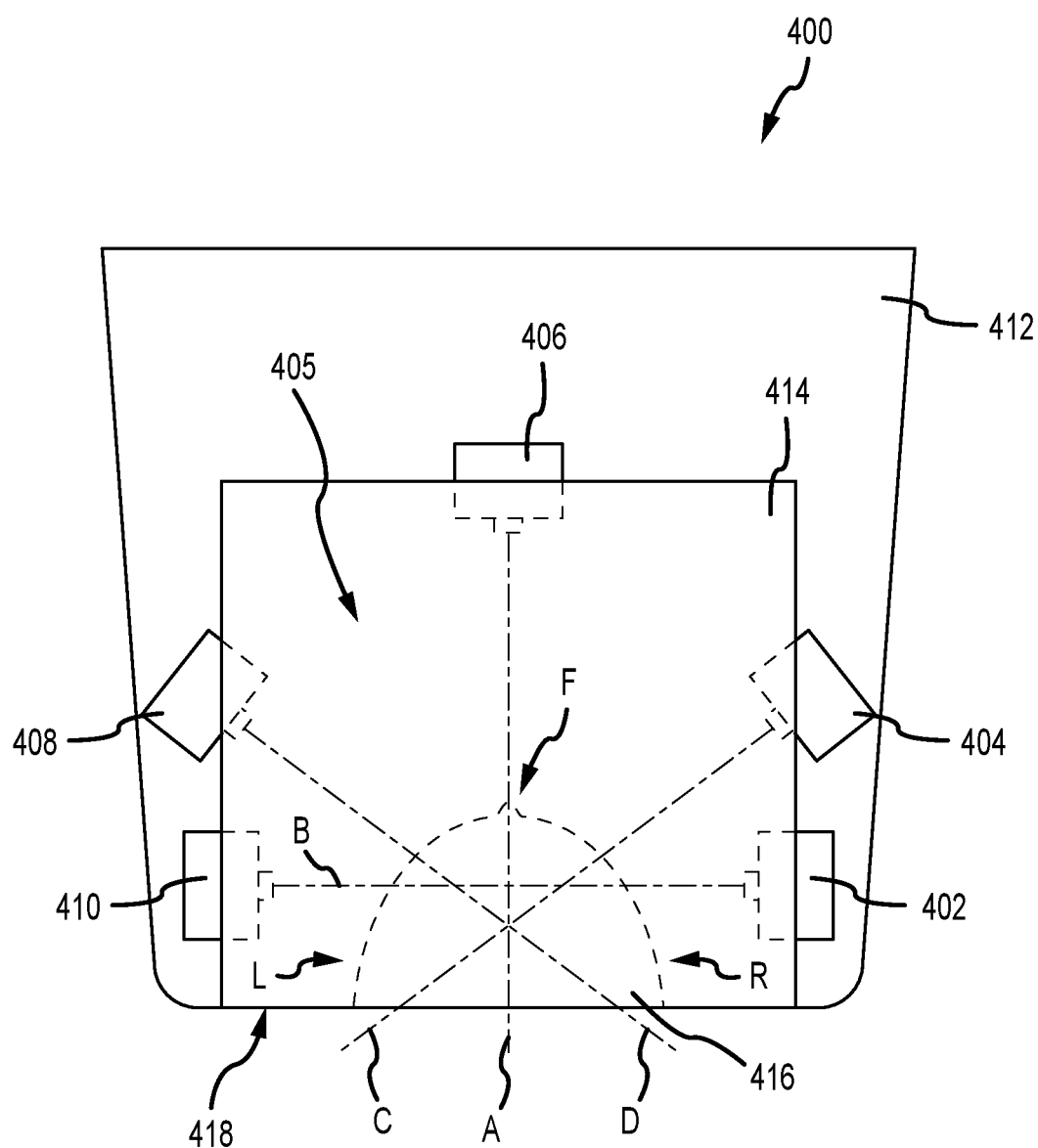
FIG. 6 is a top schematic view of a camera imaging and display system utilizing multiple cameras.

FIG. 6 is a top schematic view of a camera imaging and display system 400 utilizing multiple cameras 402-410. FIG. 6 depicts a breast support platform 412 and a breast compression paddle 414. These components compress a breast 416 there between. Five cameras 402-410 are depicted in various positions and orientations generally around and pointing towards the compressive volume 405. This figure is illustrative of various positions and orientations in which cameras 402-410 may be disposed. Multiple cameras may be used to capture images of various portions of the breast 416 and only a few particular arrangements are described. Other positions and orientations are contemplated. For context, the description of FIG. 6 begins with camera 406 which may be axially aligned along axis A with the breast 416 (e.g., at the nipple thereof). Axis A is also substantially orthogonal to a front wall 418 of the support platform 412 (and/or the compression paddle 414). In this position and orientation, images primarily of the front portion F of the breast 416 may be obtained by camera 406. Further, depending on the mounting height of the camera 406, images of all or part of the upper surface of the breast 416 may also be obtained. Regardless, if additional images are desired, other cameras positioned in other positions and orientations may be utilized.

Cameras 402, 410, for example, may be used to capture images of the right side portion R and the left side portion L of the breast 416, respectively. These cameras 402, 410 may be arranged along an axis B that is substantially orthogonal to axis A and may be parallel to the front wall 418. When utilized in conjunction with camera 406, a considerable amount of the front F and side portions L, R of the breast may be imaged. Cameras 404, 408 may also be used to capture the right side portion R and the left side portion L of the breast 416, respectively. Cameras 404, 408 are disposed such that their lines of sight (along axes C and D, respectively) are both non-parallel and non-orthogonal to each of axis A, axis B, and front wall 418. This configuration enables cameras 404, 408 to capture images of all or part of the front portion F of the breast 416. In such a case, it is possible that cameras 404, 408 may be able to capture images of the entire periphery of the breast 416. In examples, one or more of the cameras 402-410 may be positioned as to extend upwards from the support platform 412. In other examples, one or more of the cameras 402-410 may be secured to the compression paddle 414 or compression arm (not shown). In another example, one or more of the cameras 402-410 may be secured to the compression paddle 414, so as to hang at or slightly beneath the bottom-most surface of the foam compressive element (not shown). Further, as described above with regard to FIG. 5, portions of the foam compressive element may be cut away, removed, or otherwise not present so as to improve line of sight from a camera 402-410 to the breast 416. Regardless of position, it is desirable that the cameras 402-410 are disposed outside the field of emission of the x-ray source, so as to prevent generation of artifacts in the resulting x-ray images.

Figure 7:
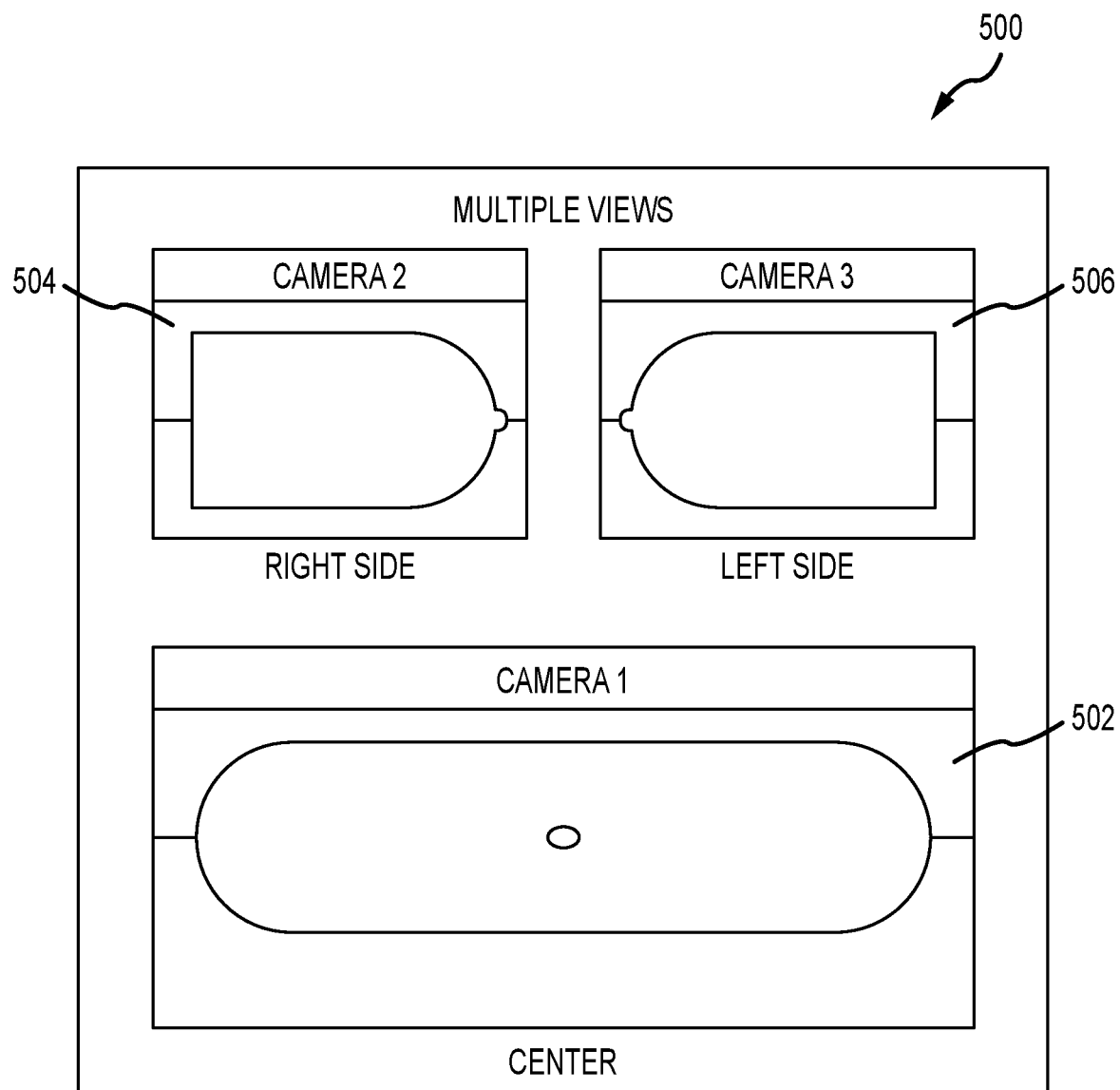
FIG. 7 is a schematic view of an example display for a camera imaging and display system.

FIG. 7 is a schematic view of an example display 500 for a camera imaging and display system. As described above, the display 500 may display images 502, 504, 506 captured by multiple cameras. As an example, if cameras 406, 402, and 404 from FIG. 6 are utilized, images 502, 504, and 506 respectively, may be displayed. Information for each displayed image (e.g., camera position, camera number, etc.) may be displayed in conjunction with each image 502, 504, 506. When visualized together, a technologist positioning the breast may accurately position the breast.

Figure 8:
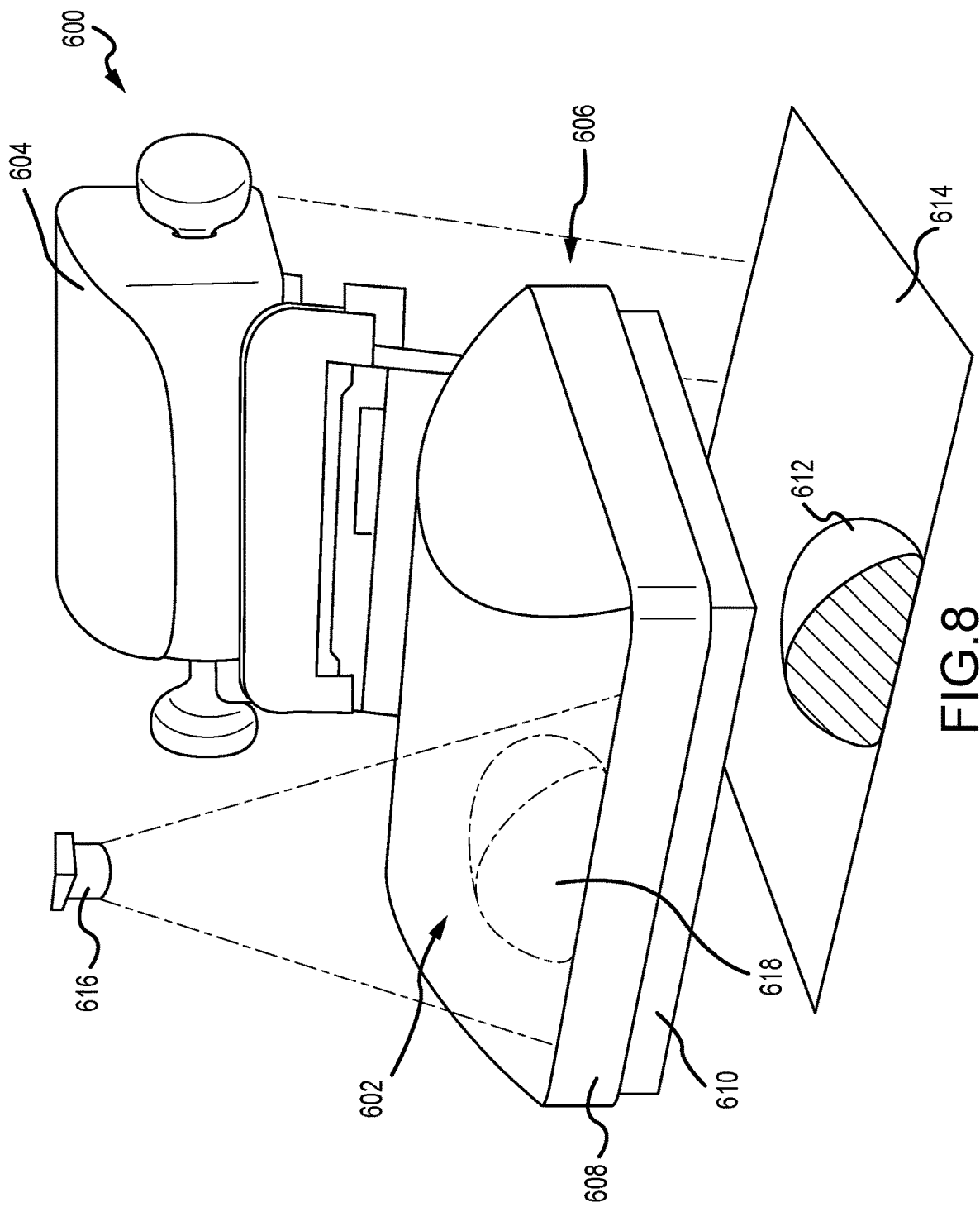
FIG. 8 is a partial perspective view of an imaging system utilizing another example of a display.

FIG. 8 is a partial perspective view of an imaging system 600 utilizing another example of a display 602. The imaging system 600 includes, in relevant part, a compression arm 604 that is connected to a compression paddle 606. The compression paddle 606 includes a rigid substrate 608 to which a thick foam compressive element 610 is secured. The display 602 in this example, is a convex surface disposed on the rigid substrate 608. Images are captured by various cameras (not shown) disposed at various locations around the breast 612 that is supported by the support platform 614. A projector 616 disposed on the tube head projects the captured images down onto the display 602. Prior to projection, however, the images may be processed such that the edges of various discrete images may be stitched together using known image processing techniques. In another example, multiple projectors may each project a discrete image. The convex display 602 mimics somewhat the curvature of the breast 612 disposed below the foam compressive element 610. This provides a more realistic representation 618 of the breast 612, thus allowing the compression paddle 602 to appear almost "transparent," allowing for greater ease in positioning the breast 612.

Figure 9:
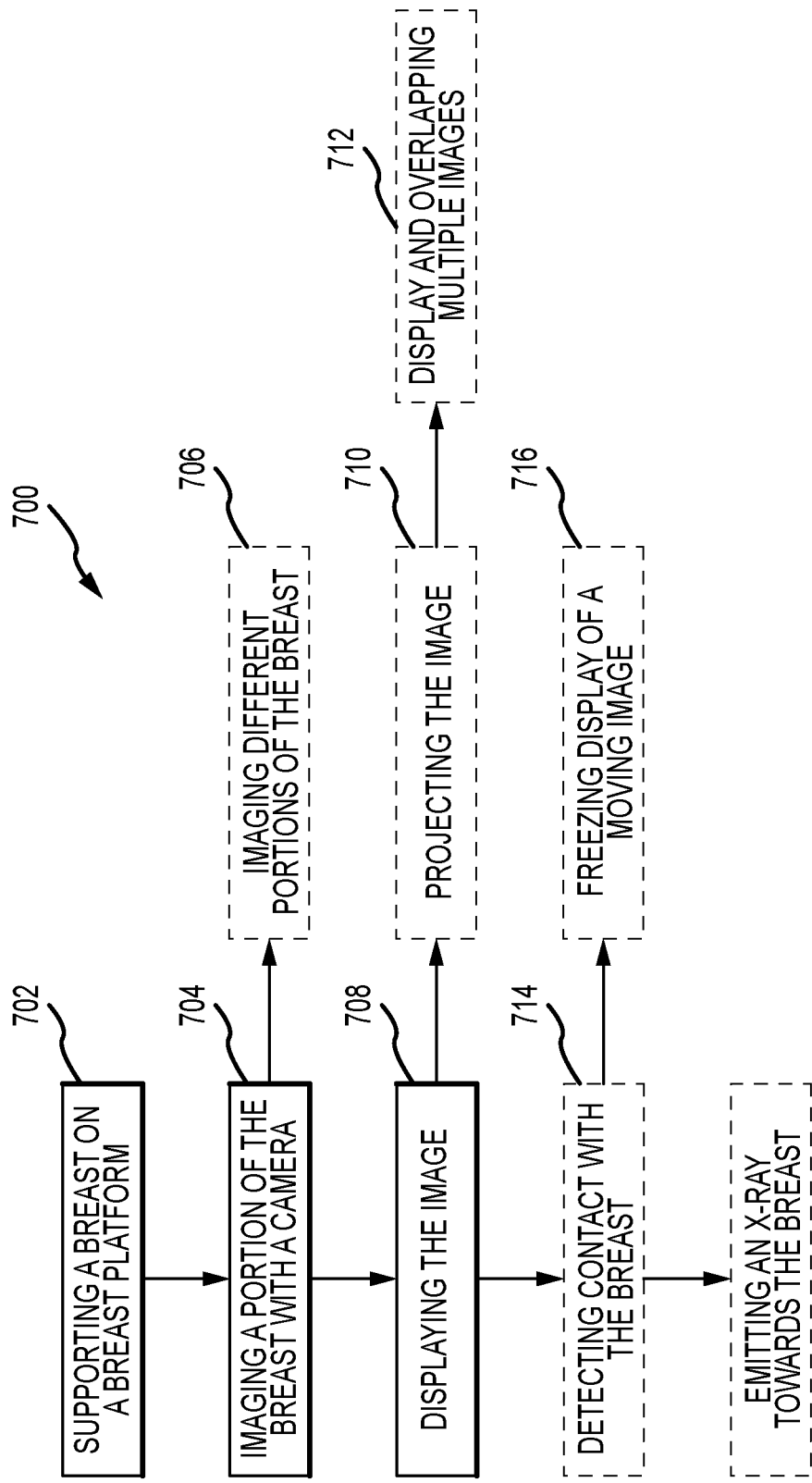
FIG. 9 depicts a method of displaying an image of a breast in a breast compression system.

FIG. 9 depicts a method 700 of displaying an image of a breast in a breast compression system of a breast imaging system. Both breast imaging systems and the compression systems incorporated therein are described elsewhere herein. In brief, the breast compression system includes a breast support platform and a breast compression paddle. The method 700 begins with supporting the breast on the breast support platform, operation 702. Once supported, the method 700 continues with imaging at least a portion of the breast with at least one camera disposed on the breast compression system, operation 704. In certain examples, a plurality of cameras may be utilized. In such a system, each camera may image different portions of the supported breast; as such, imaging a portion of the breast may include imaging different portions of the breast with the cameras to obtain a plurality of images, operation 706. Next, displaying an image, operation 708, is performed. In examples, displaying an image 708 contemplates displaying the image on a display. In other examples, displaying an image includes projecting the image onto a screen, operation 710. In examples where multiple images are obtained, those images may be displayed discretely (as depicted in FIG. 7), or adjacent portions of the images may be displayed and overlapped, operation 712 (as depicted in FIG. 8).

As described elsewhere herein, the multiple images may be images of top surfaces, side surfaces, front surfaces, etc. of the breast. In fact, the cameras may be disposed in any location as required or desired for a particular purpose. In examples, the images captured may be moving images, although still images may also have value, for example, to preserve the position of the breast when contact is made with the compression paddle. Thus, detecting contact between the breast and the paddle, operation 714, may be desirable. And, upon contact, freezing the display may be performed, operation 716. Once the breast is stabilized by the compression paddle, imaging the breast may be performed. In the case of systems that utilize a screen on the compression paddle, along with a projector, x-ray images may be emitted towards the breast and through the screen, operation 718. This may occur in certain examples based on the contact detected in operation 714.

Figure 10:
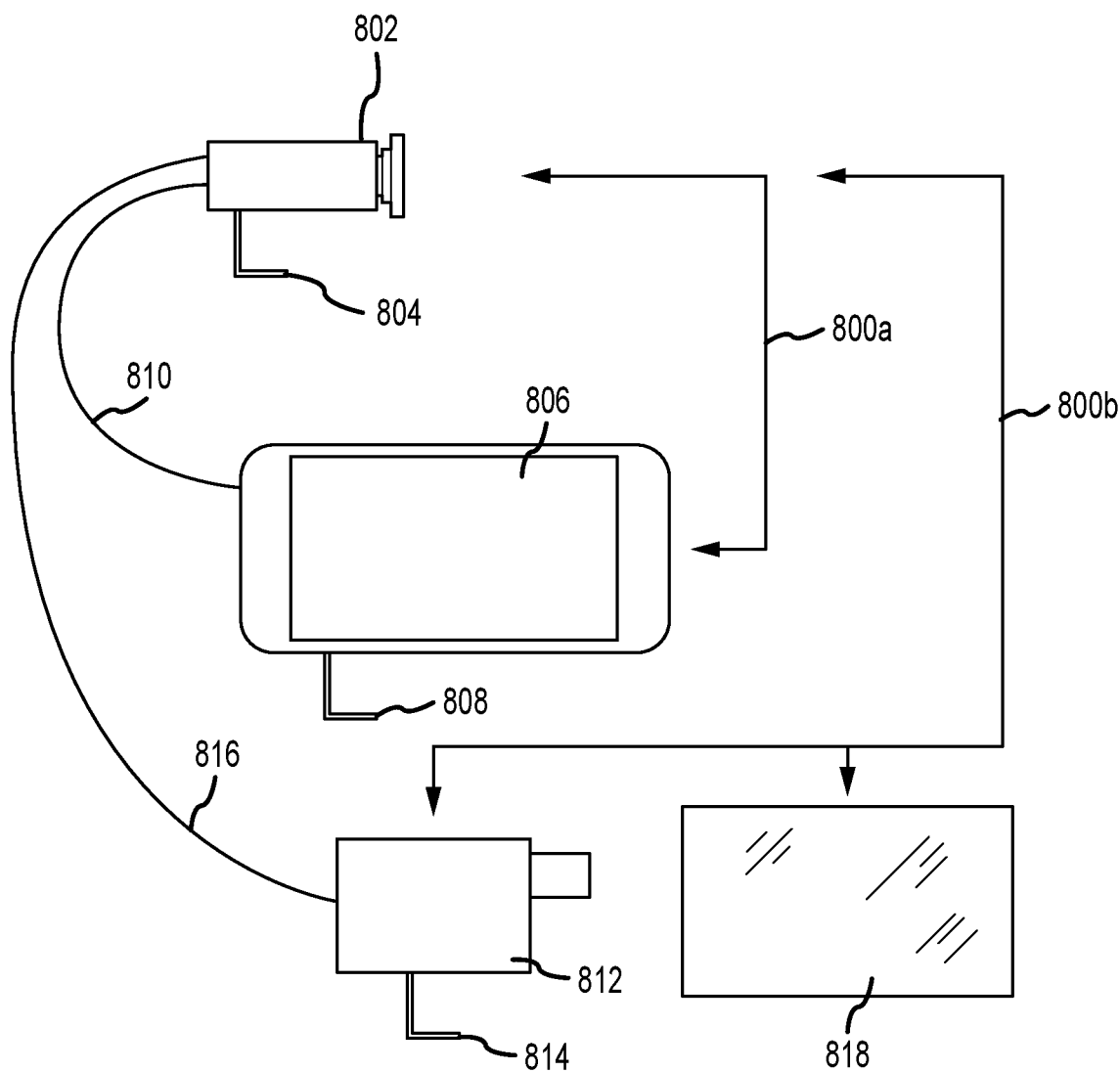
FIG. 10 depicts an upgrade system for a breast x-ray imaging system.

FIG. 10 depicts two upgrade systems 800a, 800b for a breast x-ray imaging system, for example, as depicted in FIGS. 1A and 1B. The upgrade systems 800a, 800b allow existing breast imaging systems to be enhanced without significant redesign. Upgrade system 800a is described first. The system 800a includes a camera 802 and a bracket 804 for connecting the camera to a compression assembly (e.g., the support arm, compression paddle, and/or breast support platform). The system 800a also includes a display 806 and a securement element 808 for connecting the display 806 to the breast imaging system. In examples, the display 806 may be attached via the securement element 808 (e.g., a bracket) to the compression arm, gantry, support arm, compression assembly, or other component as depicted and described elsewhere herein. The display 806 may be an LCD or LED screen. The camera 802 may be connected to the display 806 via a wired or wireless connection, depicted as line 810 in FIG. 10.

The upgrade system 800b includes a camera 802 and a bracket 804 for connecting the camera to a compression assembly (e.g., the support arm, compression paddle, and/or breast support platform). The system 800b also includes a display 812 and a securement element 814 for connecting the display 812 to the breast imaging system. In this example, the display 812 is a projector that may be attached via the securement element 814 (e.g., a bracket) to the tube head of the imaging system as depicted and described elsewhere herein. The camera 802 may be connected to the display 812 via a wired or wireless connection, depicted as line 816 in FIG. 10. In upgrade system 800b, the display may also includes a discrete sheet material 818 that may be secured to the compression paddle to act as a screen. The projector 812 projects the captured images at the screen.

Figure 11:
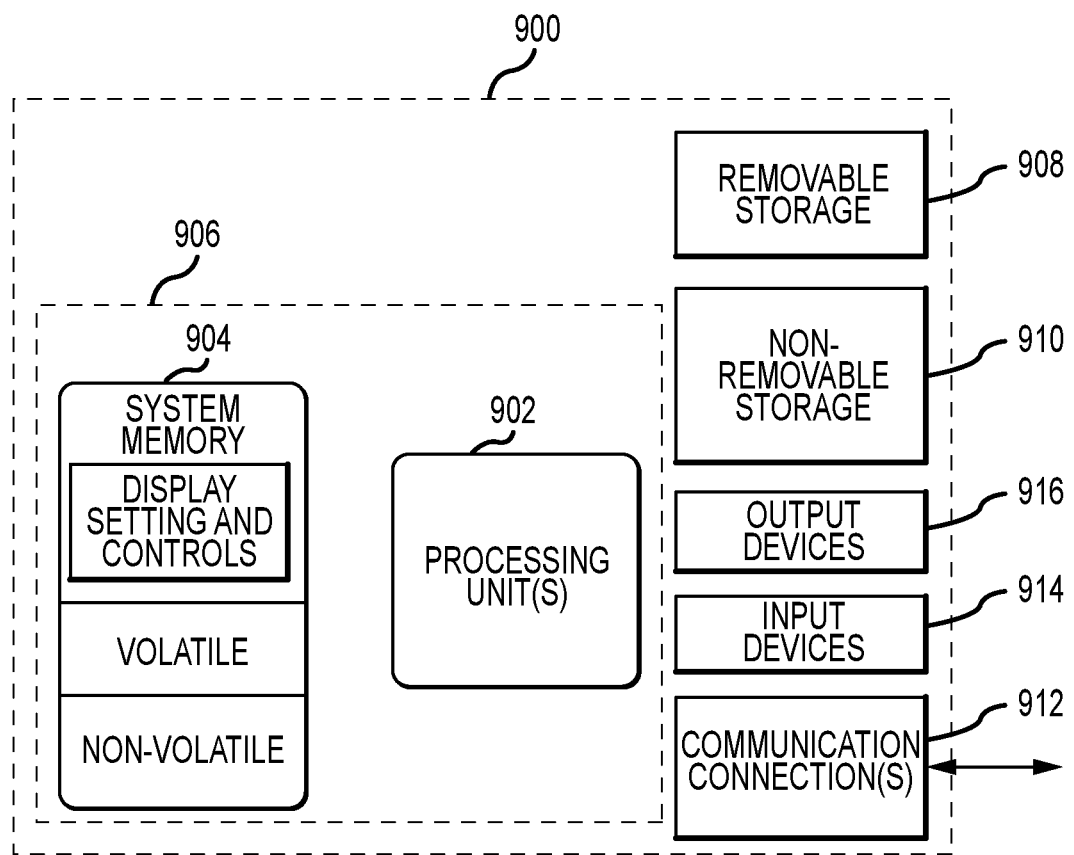
FIG. 11 depicts an example of a suitable operating environment in which one or more of the present examples can be implemented.

FIG. 11 illustrates one example of a suitable operating environment 900 in which one or more of the present examples can be implemented. This operating environment may be incorporated directly into the visualization systems disclosed herein, or may be incorporated into a computer system discrete from, but used to control the visualization systems described herein. Such as computer system may be, e.g., the work station depicted in FIG. 1A. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 900 typically includes at least one processing unit 902 and memory 904. Depending on the exact configuration and type of computing device, memory 904 (storing, among other things, instructions to control the cameras, displays, projectors, sensors, or perform other methods disclosed herein) can be volatile (such as RAM), non-volatile (such as ROM, flash memory, etc.), or some combination of the two. This most basic configuration is illustrated in FIG. 11 by dashed line 906. Further, environment 900 can also include storage devices (removable, 908, and/or non-removable, 910) including, but not limited to, magnetic or optical disks or tape. Similarly, environment 900 can also have input device(s) 914 such as touch screens, keyboard, mouse, pen, voice input, etc., and/or output device(s) 916 such as a display, speakers, printer, etc. Also included in the environment can be one or more communication connections 912, such as LAN, WAN, point to point, Bluetooth, RF, etc.

Operating environment 900 typically includes at least some form of computer readable media. Computer readable media can be any available media that can be accessed by processing unit 902 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 900 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 900 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 900 is part of a network that stores data in remote storage media for use by the computer system 900.

FIG. 12 is an embodiment of a network 950 in which the various systems and methods disclosed herein may operate. In embodiments, a client device, such as client device 952, may communicate with one or more servers, such as servers 954 and 956, via a network 958. In embodiments, a client device may be a standalone imaging system (e.g., imaging system 100 depicted in FIG. 1A) that includes all the functionality described herein. The client device may also include or incorporate a laptop, a personal computer, a smart phone, a PDA, a netbook, or any other type of computing device, such as the computing device in FIG. 11. In examples, such a client device may be connected to an imaging system. In embodiments, servers 954 and 956 may also be any type of computing device, such as the computing device illustrated in FIG. 12. Network 958 may be any type of network capable of facilitating communications between the client device and one or more servers 954 and 956. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 954 may be employed to perform the systems and methods disclosed herein, such as the methods for imaging discussed herein. Client device 952 may interact with server 954 via network 958. In further embodiments, the client device 952 may also perform functionality disclosed herein, such as scanning and image processing, which can then be provided to servers 954 and/or 956.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A system for imaging a breast, the system comprising:
a gantry;
a tube head rotatably coupled to the gantry;
an x-ray source disposed within the tube head;
a support arm movably coupled to the gantry, wherein the support arm comprises a breast support platform;
an x-ray detector disposed within the breast support platform;
an immobilization arm movably coupled to the support arm;
an immobilization paddle coupled to the immobilization arm, wherein the breast support platform and the immobilization paddle at least partially define an immobilization volume for immobilizing a breast;
at least one camera disposed adjacent an interface between the support arm and the breast support platform and arranged so as to capture images of the immobilization volume; and an image display at least partially disposed on the system, wherein the image display is configured to display the images of the immobilization volume captured by the at least one camera.

2. The system of claim 1, wherein the image display comprises at least one of an LED display, an LCD display, and a screen.

3. The system of claim 2, wherein the image display comprises the screen and the system further comprises a projector disposed on at least one of the tube head and the support arm.

4. The system of claim 3, wherein the screen is substantially convex.

5. The system of claim 1, wherein the at least one camera comprises a plurality of cameras.

6. The system of claim 1, wherein the at least one camera is secured to at least one of the support arm, the immobilization arm, and the immobilization paddle.

7. The system of claim 5, wherein the plurality of cameras are distributed along an edge of the immobilization volume.

8. The system of claim 3, wherein the projector comprises a plurality of projectors.

9. The system of claim 3, wherein the screen is disposed on the immobilization paddle, along a path of an x-ray emitted from the x-ray source.

10. A method of displaying an image of a breast in a breast immobilization system having a breast support platform and an immobilization paddle, the method comprising:
   supporting the breast on the beast support platform;
   imaging at least a portion of the supported breast with at least one camera disposed on the breast immobilization system adjacent the breast support platform; and
   displaying at least a portion of the image, wherein the image is a moving image.

11. The method of claim 10, wherein the image is displayed on a display.

12. The method of claim 10, wherein displaying the image comprises projecting the image to a screen.

13. The method of claim 10, wherein the at least one camera comprises a plurality of cameras and wherein the imaging operation comprises imaging different portions of the supported breast with the plurality of cameras so as to obtain multiple images.

14. The method of claim 13, wherein the displaying operation comprises displaying the multiple images and at least partially overlapping adjacent portions of the multiple images.

15. The method of claim 14, wherein the multiple images comprise images of at least a top surface and at least a side surface of the breast.

16. The method of claim 10, further comprising detecting contact between at least a portion of the immobilization paddle and the breast.

17. The method of claim 16, wherein the image is a moving image and wherein the method further comprises freezing display of the moving image based at least in part on the detected contact.

18. The method of claim 16, further comprising emitting an x-ray towards the breast based at least in part on the detected contact.

19. An upgrade system for a breast x-ray imaging system comprising a tube head having an x-ray source, a support arm having a breast support platform with an x-ray detector, and an immobilization arm moveably coupled to the support arm, the upgrade system comprising:
   an immobilization paddle configured to couple to the immobilization arm, wherein when the immobilization paddle is coupled to the immobilization arm, the breast support platform and the immobilization paddle at least partially define an immobilization volume for immobilizing a breast;
   at least one camera configured to couple adjacent an interface between the support arm and the breast support platform and arrangeable to capture images of the immobilization volume; and
   a display configured to display the images of the immobilization volume captured by the at least one camera.

20. The upgrade system of claim 19, wherein the display comprises at least one of an LCD screen and an LED screen, and wherein the upgrade system further comprises a securement element for connecting the display to at least one of the immobilization arm and the immobilization paddle.

21. The upgrade system of claim 19, wherein the display comprises a projector, and wherein the upgrade system further comprises a securement element for connecting the projector to the tube head.

22. The upgrade system of claim 19, further comprising a sheet material securable to the immobilization paddle.

* * * * *